United States Patent [19]

Keith et al.

[11] Patent Number: 4,762,784
[45] Date of Patent: Aug. 9, 1988

[54] FERMEMTATION PROCESS FOR THE HIGH LEVEL PRODUCTION OF BOVINE GROWTH HORMONE

[75] Inventors: Paula M. Keith, West Terre Haute; Wendy J. Cain, Terre Haute, both of Ind.

[73] Assignee: International Minerals & Chemical Corp., Ind.

[21] Appl. No.: 754,578

[22] Filed: Jul. 15, 1985

[51] Int. Cl.⁴ .................. C12P 21/02; C12N 15/00
[52] U.S. Cl. ..................... 435/70; 435/172.3; 435/818; 935/43; 935/13
[58] Field of Search ............... 435/172.3, 68, 70, 813, 435/818; 935/43, 13

[56] References Cited

U.S. PATENT DOCUMENTS 4,167,450 9/1979 Chesbro et al. ............... 435/813
4,317,882 3/1982 Horiguchi et al. ............. 435/818
4,569,790 2/1986 Koths .......................... 435/68

FOREIGN PATENT DOCUMENTS 0103395 3/1984 European Pat. Off.

OTHER PUBLICATIONS

Queen, J. of Molecular and Applied Genetics, vol. 2, pp. 1–10, 1983.
Hopkins, Chemical Abstracts, vol. 95:148688n, 1981.
E. Keshet et al., *Nucleic Acids Research*, 9:19–30 (1981).
P. H. Seeburg et al., *DNA*, 2:37–45 (1983).
B. E. Schoner et al., *Proc. Natl. Acad. Sci. USA*, 81:5403–5407 (1984).
S. Bauer et al., *Biotechnology and Bioengineering*, vol. XVI, pp. 933–941 (1974).
J. Shiloach et al., *Biotechnology and Bioengineering*, vol. XVII, pp. 227–239 (1975).
S. Bauer et al., *Biotechnology and Bioengineering*, vol. XVIII, pp. 839–846 (1976).

*Primary Examiner*—Alvin E. Tanenholtz
*Attorney, Agent, or Firm*—Bernard, Rothwell & Brown

[57] ABSTRACT

A high density fermentation process for high yield production of bovine growth hormone by transformant *E. coli* is described. The process employs transformant strains of *E. coli* containing an expression vector coding for bovine growth hormone under the control of a bacteriophage lambda promoter-operator and a plasmid containing the λcI857 gene which codes for the temperature-sensitive repressor protein. In the initial growth period, the level of dissolved oxygen in the fermentation medium is maintained at about 20% to 60% saturation and the temperature of the medium is kept at 26°–30° C. Production of bovine growth hormone is then induced by raising the temperature of the medium to at least about 42° C. The temperature is then reduced to about 38° C. to 41° C. to optimize cell growth for the remainder of the induction period, during which the level of dissolved oxygen in the medium is maintained at about 10% to 40% saturation.

20 Claims, 2 Drawing Sheets

FERMEMTATION PROCESS FOR THE HIGH LEVEL PRODUCTION OF BOVINE GROWTH HORMONE

BACKGROUND OF THE INVENTION

This invention relates to high level microbial production of bovine growth hormone through recombinant DNA technology. This high level production is achieved through high-density fermentation of *E. coli* cells transformed with a recombinant vector carrying a gene encoding bovine growth hormone.

Bovine growth hormone (BGH) is a protein of 191 amino acids, which is initially synthesized in the anterior pituitary land as a precursor "pre-growth hormone" having 26 additional amino acids attached at the N-terminus. This 26-amino acid "signal sequence" is processed off during secretion from the pituitary cells, yielding the mature hormone. Field trials using BGH purified from pituitary glands demonstrated increased milk production and improved feed-to-milk conversion in cows to which the hormone was administered (Machlin, L. J., *Journal of Dairy Science*, 56:575–580 [1973]). The potential economic value of this hormone sparked interest in obtaining BGH in commercial quantities at reasonable cost.

Thus, much work in recent years has focused on obtaining microbial synthesis of this commercially valuable hormone using recombinant DNA technology. Gene closing and manipulation techniques well known in the art have been used to produce recombinant expression vectors containing BGH-encoding cDNA fused to regulatory regions capable of directing synthesis of BGH in the desired host cells. Microorganisms transformed with these expression vectors have been shown to produce the desired hormone. For example, Keshet et al., (*Nucleic Acids Research*, 9:19-30 [1981]) reported the cloning and low level expression in *E. coli* of a full length BGH polypeptide as a fusion protein with a portion of pBR322-encoded β-lactamase. In European Patent Application Publication No. 0 103 395, construction of several expression vectors, including vectors encoding BGH polypeptides with varying portions of the amino-terminal end deleted, is described. BGH polypeptides with varying portions of the amino-terminal end of the mature hormone deleted were found to retain biological activity and to be expressed at much higher levels than was the complete hormone in the expression systems described. Yields of BGH in various *E. coli* strains transformed with the expression vectors (and also with a plasmid carrying a gene encoding a temperature-sensitive repressor to control BGH synthesis) were 100 mg/liter or less in small-scale cultures. Large-scale fermentation of the transformed strains is not reported. Seeburg et al., (*DNA*, 2:37–45 [1983]) describe the cloning of bovine and porcine growth hormone cDNA and construction of expression vectors encoding the complete mature hormones (i.e., the "pre" or signal sequence region is removed in vitro during vector construction). *E. coli* cells were transformed with the BGH expression vector and BGH synthesis was regulated by the plasmid-borne *E. coli* trp regulatory region. It is reported that high density fermentation of the transformed *E. coli* cells yielded approximately 1.5 grams/liter BGH, but no description of the fermentation conditions is given.

Obtaining maximum expression levels of the protein products of cloned genes often involves some trial and error. The genes may be fused to several different regulatory regions and/or transformed into several host cell strains for comparative analyses to find the transformed strain giving the highest production levels of the desired protein. To date, efforts at yield improvement of microbially produced growth hormones have been carried out primarily at the level of genetic manipulations designed to increase cellular expression. There is still a need for the development of commercial scale fermentation processes capable of producing growth hormones in the highest possible yields.

SUMMARY OF THE INVENTION

The present invention provides a method of producing BGH at high levels by fermentation of *E. coli* cells transformed with a recombinant vector containing a BGH-encoding gene under conditions which optimize the yield of BGH. BGH expression is regulated by a temperature-sesitive repressor encoded by a second plasmid which has also transformed the *E. coli* host strain. Using the method of the present invention, we have obtained high density fermentations yielding BGH at 3.6 to 5.9 grams per liter.

This method of producing BGH comprises inoculating an aqueous fermentation medium with a transformant *E. coli* strain containing an expression vector which directs the expression of bovine growth hormone under the control of a phage lambda promoter-operator and an expression vector which directs the expression of the λcI857 temperature-sensitive repressor protein. The transformant strain is grown in the fermentation medium for an initial growth period during which the level of dissolved oxygen in the medium is maintained at from about 20% to 60% of saturation and the temperature of the medium is maintained at between about 26° C. and 30° C. This initial growth period is followed by an induction period during which BGH synthesis is induced by raising the fermentation medium temperature to at least about 42° C. to inactivate the temperature-sensitive cI857 repressor protein, then reducing the temperature to about 38° C. to 41° C., preferably about 40° C., and continuing to grow the transformant strain, for the remainder of the induction period with the dissolved oxygen level in the medium maintained at from about 10% to 40% of saturation. The bovine growth hormone thus produced is then recovered from the transformant cells.

DETAILED DESCRIPTION OF THE INVENTION

Figure 1:
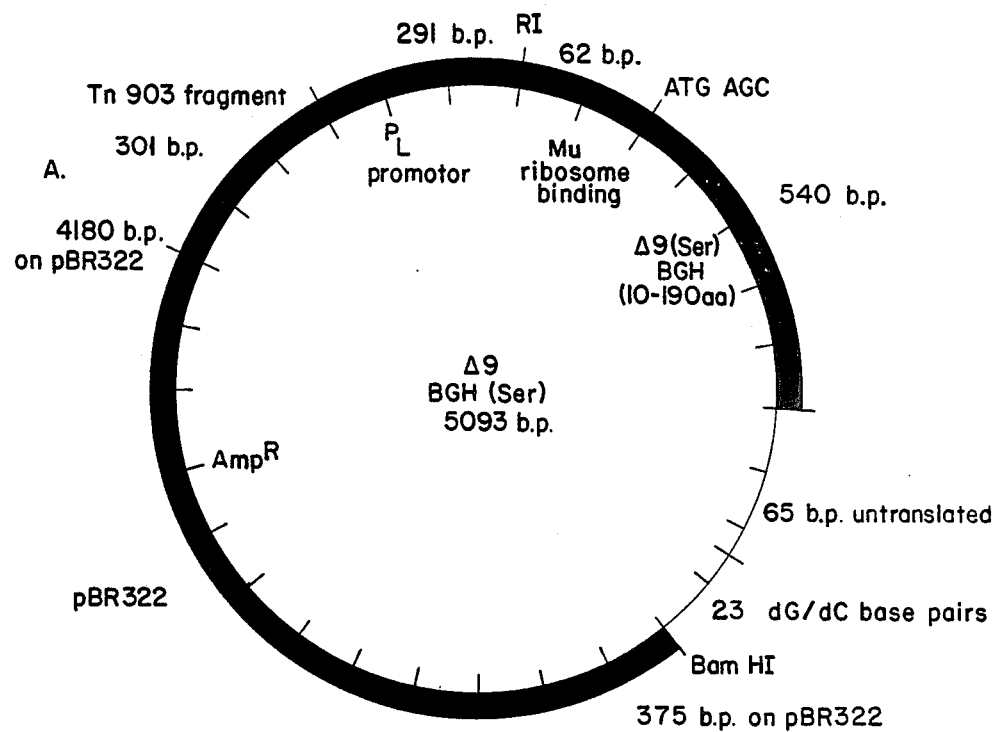
FIG. 1 is a representation of the salient features of plasmid $P_L$-mu-Δ9 (Ser) BGH, a BGH expression vector which can be used in the method of the invention.

We have developed a method of enhancing BGH production in an *E. coli* strain transformed with a BGH-encoding plasmid. The plasmid which directs BGH expression in the method of the invention can be any suitable BGH-encoding plasmid in which BGH expression is directed by a regulatory region comprising a promoter-operator region derived from bacteriophage λ, preferably the $\lambda P_L$ promoter-operator region. The regulatory region also contains a Shine-Dalgarno (ribosomal binding) region, which is preferably derived from bacteriophage mu. The BGH-encoding sequence, which is operably fused to the regulatory region, comprises a DNA sequence encoding a polypeptide having the amino acid sequence of BGH or a biologically active fragment or analog thereof. As used herein, the terms "bovine growth hormone" and "BGH" include fragments of the hormone which may, for example, have varying portions of the amino terminal end of the hormone deleted, or may have various substitutions or modifications in the BGH sequence which do not destroy the biological activity of the polypeptide. BGH polypeptides lacking various portions of the amino terminal end of the hormone have been shown to retain biological activity. In a preferred embodiment of the invention, the BGH-encoding plasmid encodes Δ9 BGH, i.e., a polypeptide corresponding in amino acid sequence to BGH less the first nine amino-terminal amino acids of the mature hormone.

Advantageously, the plasmid also carries a gene encoding a selectable marker, e.g., an antibiotic resistance gene, for selection of cells transformed by the plasmid.

The transformant strain employed in the method of the invention also contains a λcI857 repressor gene. The repressor protein encoded by this temperature-sensitive mutant gene is known to interact with the operators of phage λ gene regulatory regions (including the $P_L$ operator) to prevent transcription of genes off the promoter in the regulatory region.

This repressor protein has been used to regulate synthesis of desired proteins encoded by recombinant vectors in various transformant strains. For example, C. Queen (*J. of Molec. and Appl. Genetics*, 2:1 1983), H. Kupper (European Patent Application Publication No. 0 076 037) and G. Buell (European Patent Application Publication No. 0 103 395) all describe the use of the cI857 repressor to regulate synthesis of a recombinant vector-encoded desired protein. The cI857 gene is either carried on the vector carrying the gene for the desired protein (and the λ promoter-operator region directing its expression) or on a separate plasmid transformed into the host cells. Synthesis of the desired protein was repressed by cultivating the transformant host cells at temperatures between 28° C. and 32° C. until the desired cell density was reached. These investigators then inactivated the cI857 repressor (thus inducing synthesis of the desired protein) by raising the temperature to 42°–43° C. for the remainder of the cultivation period.

The cI857 gene is used in the method of the invention to control BGH synthesis, and may be carried in the host cell chromosome, on the BGH-encoding plasmid, or on a second plasmid. In a preferred embodiment of the invention, a second plasmid which directs expression of the cI857 repressor protein is transformed into the host strain along with the BGH-encoding plasmid. We have observed that the cI857 repressor interacting with the λ$P_L$ promoter-operator is inactivated to some degree at temperatures as low as 37° C., as evidenced by inclusion body formation (indicating BGH synthesis) in shake flask cultures. The best results were achieved, however, by inactivating the cI857 repressor by raising the temperature to 42° C. for 1 hour, then lowering it to 40° C. for the remainder of the fermentation.

The host cells may be any transformable *E. coli* strain suitable for high density fermentation and in which the expression vectors used to transform the cells will be stably maintained. Many such strains are known in the art, with one suitable strain being *E. coli* HB101 (Leu Lac pro thi hrs hsm supE recA sm$^r$).

A preferred transformant strain for use in the method of the invention is *E. coli* HB101 ($P_L$-mu-Δ9 (Ser) BGH and pcI857). Construction of an *E. coli* transformant containing these plasmids is described in European Patent Application Publication No. 0 103 395, hereinafter referred to as EPO 0 103 395, the disclosure of which is incorporated herein by reference. *E. coli* HB101 ($P_L$-mu-Δ9 (Ser) BGH and pcI857) has been deposited, with the designation *E. coli*, IMC No. 1, at the American Type Culture Collection, Rockville, Md., with accession no. 53030. It will be appreciated, however, that the method of the invention is equally applicable to obtain high level production of BGH using other transformant strains in which BGH expression is under control of the cI857 gene product.

Plasmid $P_L$-mu-Δ9 (Ser) BGH, represented in FIG. 1, encodes a BGH polypeptide lacking the first nine amino-terminal amino acids of the mature hormone and containing an additional serine residue, not normally present in BGH, at the N-terminus. The additional serine residue is present as an artifvact of genetic manipulation at the 5' end of the gene. Expression of the BGH-encoding sequence is controlled by a regulatory region comprising the phage λ$P_L$ promoter-operator, a Shine-Dalgarno region derived from bacteriophage mu, and an initiation codon (ATG) adjacent (and 5') to the BGH sequence. The plasmid also carries a gene for ampicillin resistance.

Referring to FIG. 1, the Δ9 (Ser) BGH gene was cloned on plasmid pPLC24 (*Gene*, 15:81–93, 1981) which is a derivative of pBR322 (G. Sutcliffe, Cold Spring Harbor Symposia, 1978). Point A on the plasmid is nucleotide 4180 in the Sutcliffe sequence. Plasmid pBR322 then continues counterclockwise to the BamHI recognition site at nucleotide 375 of the pBR322 sequence. Clockwise from point A is a 301 base pair fragment from Tn903 which was inserted with the 291 base pair pL promoter. An EcoRI restriction site divides the promoter from a mu sequence which supplies the ribosome binding site up to the initiating ATG codon. In the Δ9 (Ser) BGH construction, DNA is included which codes for serine followed by amino acids 10 through 191, the final amino acid of BGH. This is followed by 65 base pairs of untranslated DNA, 23 dG/dC base pairs from the homopolymeric tails annealed during the original cloning procedure and finally the BamHI recognition site, added with synthetic DNA.

Figure 2:
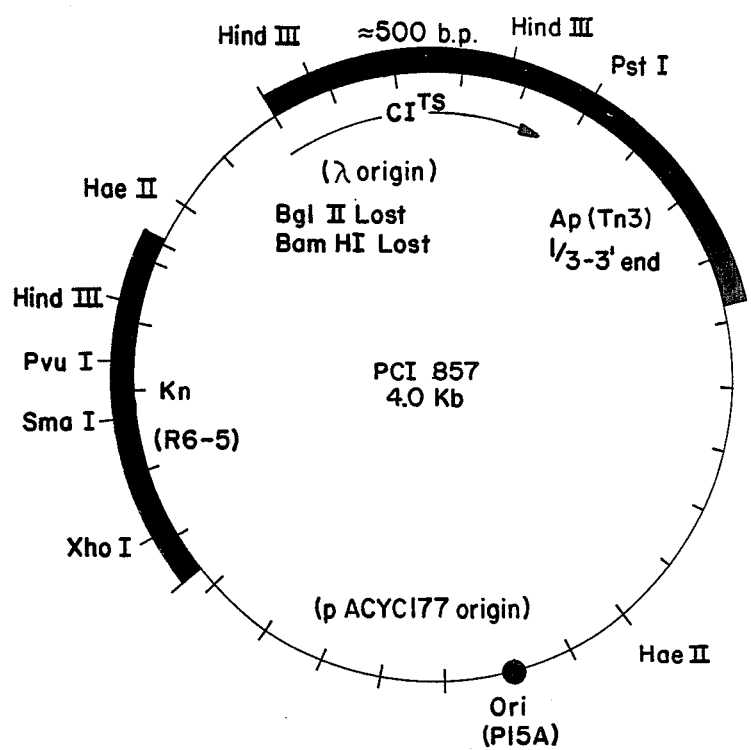
FIG. 2 is a representation of the salient features of plasmid pcI857, which encodes a temperature-sensitive repressor used to control BGH production in the method of the invention.

Plasmid pcI857, shown in FIG. 2, is a multicopy plasmid which encodes the cI857 temperature-sensitive repressor and also carries a kanamycin resistance gene. *E. coli* HB101 cells transformed with both plasmids were selected by growth in Luria broth supplemented with both ampicillin and kanamycin by a procedure similar to that described in EPO 0 103 395.

The transformant strain is used to inoculate an aqueous medium contained in a fermentor. The aqueous fermentation medium can be any medium suitable for supporting high density growth of *E. coli*. The medium contains a carbon source, a nitrogen source, salts, and any other nutrients required for cell growth. Suitable carbon sources include, among others, glycerol and hydrated glucose (available commercially as Cerelose ®). Suitable nitrogen sources include, among others, acid hydrolysates of casein (commercially available as HyCase Amino Acids or Casamino Acids); enzymatic hydrolysates of casein (NZ Amine A, Casatone, Tryptone); vegetable derived hydrolyzed proteins (soybean peptones, hydrolyzed corn gluten, cottonseed peptone); meat peptones; and yeast extracts. The foregoing list of carbon and nitrogen sources is merely exemplary of known, commercially available sources. Other suitable carbon and nitrogen sources will be readily apparent to those skilled in the art. Any components required for retention of plasmids by host cells are added to the medium. For example, the antibiotics ampicillin and kanamycin are added when the transformant strain *E. coli* HB101 ($P_L$-mu-$\Delta$9 (Ser) BGH and pcI857) is grown in a fermentor.

Any conventional fermentation equipment known in the art can be used, provided there are means of controlling the medium temperature, of agitating and aerating the medium, and of adding oxygen to the intake air.

The fermentor is inoculated with a culture of the transformant strain. Advantageously, the culture will have been previously incubated at about 30° C. for between 8 and 24 hours (or until the $A_{550}$, i.e., the absorbance at 550 nanometers, of the culture is between 4 and 10) with agitation, for example, at 200 rpm. Preferably, the culture is incubated at 30° C. for about 15 to 20 hours, or until the $A_{550}$ is between 4 and 6. The culture can be grown in any suitable medium, for example, Luria broth. The volume of culture used to inoculate the fermentor is between 1/50th and 1/20th, preferably about 1/25th of the volume of medium contained in the fermentor.

In the method of the invention, the fermentation is conducted in two phases. Following inoculation of the fermentation medium with the transformant strain, an initial growth period is conducted during which the level of dissolved oxygen in the medium is maintained at from 20% to 60% saturation, preferably at about 50% saturation. This may be accomplished by feeding ambient air into the fermentor at a rate sufficient to maintain the dissolved oxygen concentration at the desired level, while also agitating the fermentation medium by any suitable mechanical means. Feeding ambient air at a rate of 0.8 to 1.2, preferably about 1.0, volume of air (STP) per volume of liquid per minute with agitation at 800 to 1200 rpm, preferably about 1000 rpm, is suitable. The agitator is driven by a motor which preferably provides a power input of about 0.5 to 2.0 horsepower per 100 gallons of fermentation medium. The temperature of the medium during the initial growth period is any temperature at which *E. coli* growth is supported while the cI857 repressor protein is active and BGH expression in the transformant strain is therefore repressed. During the initial growth period, the temperature is preferably held between 26° C. and 30° C., most preferably at about 28° C.

The initial growth period is continued until cell density (as measured by the $A_{550}$ of a sample of culture from the fermentor) reaches 50 to 60, which commonly occurs at about 23 to 25 hours after inoculation of the fermentation medium. At this point, the second fermentation phase, an induction period, is begun. The temperature of the fermentation medium is raised to at least about 42° C. (preferably 42° C.) and held there for about one hour, thereby inactivating the cI857 repressor protein and inducing production of BGH in the transformant strain. The temperature is then reduced to about 38° C. to 41° C., preferably about 40° C. At this temperature, the cI857 repressor protein is inactive but conditions are more favorable for *E. coli* growth than at 42° C.

The dissolved oxygen level in the medium is maintained at from about 10% to 40% of saturation during the induction period. Any suitable means of aeration and agitation can be used to maintain this dissolved oxygen level. In a preferred embodiment of the invention, ambient air is fed at a rate of 0.8 to 1.2, preferably about 1.0, volumes of air (STP) per volume of liquid per minute, and the medium is agitated at 800 to 1200 rpm, preferably about 1200 rpm. The agitator is driven by a motor which preferably provides a power input of about 0.5 to 2.0 horsepower per 100 gallons of fermentation medium. Since the rate of oxygen consumption is increased during the induction period, it is preferred to supplement the oxygen present in the ambient air source by feeding oxygen into the fermentor in order to maintain the desired dissolved oxygen level. Any conventional means of providing oxygen to the fermentation medium may be employed. For example, a sparger which is connected to an oxygen source may be inserted directly into the medium or oxygen may be added to the ambient air being fed into the fermentor.

The induction period is continued until cell density reaches an $A_{550}$ of about 80 to 125, preferably 100 to 123. These cell densities are commonly reached at about 7 to 8 hours after the start of the induction period. Fermentation parameters indicating that BGH synthesis and cell growth are complete include: (1) a significant decrease in oxygen demand (2) no further increase in cell density ($A_{550}$ values) and (3) NaOH utilization (for pH control) stops.

Nutrients which are depleted from the fermentation medium during cell growth are replenished by any of the methods known in the art. Nutrients may be fed continually or in portions during the fermentation. Preferably, nutrients are added in portions three times during the fermentation: when the cell density reaches an $A_{550}$ of 30–35, when cell density reaches an $A_{550}$ of 50–60, and again at an $A_{550}$ of 90–100. The first feeding of nutrients takes place during the initial growth period, usually about 16 hours after inoculation. The second feeding takes place just before the temperature is raised to begin the induction period, usually about 23 to 25 hours after inoculation. The third feeding is given during the induction period, usually about 29 hours after inoculation.

The nutrients to be added will depend on the composition of the fermentation medium chosen, but will generally include a carbon source and a nitrogen source. Advantageously, the feedings comprise about equal amounts by weight of NZ Amine A and glycerol. Preferably, each of the first two feedings comprises a total of about 45–60 grams of the combined nutrients per liter of medium in the fermentor and the third feeding comprises a total of about 20–25 grams of the combined nutrients per liter of medium. We achieved excellent results by adding 250 grams each of NZ Amine A and glycerol in one liter of water to 9.4 liters of fermentation medium at 16 hours post-inoculation and adding another 250 grams each of NZ Amine A and glycerol in one liter of water to the fermentation medium at 24 hours post-inoculation. We then added 125 grams each of NZ Amine A and glycerol in one liter of water to the fermentor at 29 hours post-inoculation.

The BGH produced by the transformant strain may be recovered by any suitable means known in the art. Cells may be harvested from the fermentation medium by, for example, centrifugation. Cells are then lysed by enzymatic, chemical or mechanical means, for example, using sonication, a French press, or treatment with such agents as lysozyme and detergents such as Triton-X-100. BGH may be purified from the cell lysate by any suitable protein purification method, including affinity chromatography, selective precipitation from a solution of a salt such as ammonium sulfate, ion exchange chromatography, isoelectric focusing, or any combination of methods.

The fermentation process of the invention has yielded 3.6 to 5.9 grams per liter of Δ9 (Ser) BGH in high density fermentations. Investigators who previously have worked with E. coli hosts transformed with $P_L$-mu-Δ9 (Ser) BGH and pcI857 reported yields of 100 mg/liter Δ9 BGH or less from small cultures, as measured by radioimmunoassay (see EPO 0 103 395). Using the method of the present invention, we have successfully enhanced the BGH production levels achieved using this transformant strain.

The method of the invention is described more fully in the example which follows. The example is provided to further illustrate the method of the invention and is not to be construed as limiting the scope of the invention.

EXAMPLE I

Conditions for Enhanced Microbial Production of Bovine Growth Hormone

Samples of E. coli HB101 ($P_L$-mu-Δ9 (Ser) BGH and pcI857) cells, ATCC 53030, to which 10% (v/v) glycerol had been added, were stored under liquid nitrogen or at −85° C. until needed.

The inoculum for a 9-liter fermentor charge was obtained by adding the cells to duplicate 500 ml baffled flasks each containing 200 mL of LB medium. The LB medium had the following composition: 10 g per liter tryptone, 5 g per liter yeast extract, 10 g per liter NaCl, 100 μg/ml ampicillin plus 50 μg/ml kanamycin. The pH of the medium was adjusted to a value of 7.0. The flasks were closed with a milk filter closure so that some aeration of the medium could take place while the flasks were shaken at 200 rpm for 15-20 hours at 30° C. in a New Brunswick shaker (until the $A_{550}$ reached 4–6).

The fermentor was a New Brunswick Microgen with a total volume of 16 liters. Nine liters of liquid medium were initially charged to the fermentor plus 400 ml of inoculum.

Fermentation Medium

The composition of the initial 9 liters of medium is shown below:

| Product | Concentration (Grams/Liter) |
| --- | --- |
| NZ Amine A-Sheffield | 33.0 |
| Glycerol | 55.0 |
| $(NH_4)_2SO_4$ | 5.6 |
| $K_2HPO_4$ | 6.7 |
| $NaH_2PO_4$ | 3.3 |
| Na Citrate | 1.1 |
| $MgSO_4.7H_2O$ | 7.8 |
| Hodag K-67 Antifoam | 5 ml |
| $FeCl_3.6H_2O$ | 0.014 |
| ZnO | 0.0014 |
| $CuCl_2.2H_2O$ | 0.00028 |
| $Co(NO_3)_2.6H_2O$ | 0.00028 |
| $(NH_4)_2Mo\ O_4$ | 0.00028 |
| EDTA (disodium salt) | 0.14 |

The medium was sterilized at 15 psig steam pressure (121° C. for 15 to 20 minutes) and the pH was adjusted to 6.8 with NaOH. The pH was maintained by additions of NaOH, as necessary, during fermentation.

To the medium, ampicillin and kanamycin were added in sufficient amount to give a concentration of 25 mg/L for each antibiotic. The solution of antibiotics was sterilized by filtration.

During the fermentation, three additional feedings of nutrients were added to the fermentor. The first feeding (at an $A_{550}=30$-35) consisted of 250 g of NZ Amine A and 250 g of glycerol dissolved in one liter of water. This allowed the cell density to increase to $A_{550}$ of 50-60 before temperature induction. At cell densities of 50-60 (23–25 hours after inoculation), the fermentor was again fed 250 g NZ Amine A plus 250 g glycerol and the bacteria were induced to synthesize BGH by raising the temperature to 42° C. for one hour. At an $A_{550}$ of 90–100, a final feeding of 125 g NZ Amine A plus 125 g glycerol was added so that nutrients were available for the remaining induction period.

Dissolved oxygen (DO) concentration was constantly monitored throughout the fermentation with a galvanic probe connected to a strip recorder. During induction, DO was maintained at 10–40% saturation (1–4 ppm) by enriching the inlet air with oxygen gas. A gas tank equipped with an oxygen regulator was used to control the flow of oxygen into the inlet air. After the gases were mixed, the oxygen-enriched air was filtered and entered the fermentor vessel through a sparger.

Fermentor Operation

The operating conditions that gave the best results are set forth in this section.

1. Time Period: 0–24 Hours
   a. Temperature of medium=28° C.
   b. Agitator speed: 1000 RPM.
   c. Energy input by agitator: 1.0–2.0 horsepower per 100 gallons.
   d. Aeration rate: 10 L (STP) per minute.
   e. Back pressure: 3 lbs per $in^2$.
   f. Dissolved oxygen: 50% of saturation value.
   g. Additional feeding at 16 hours ($A_{550}=30$-35.)
   h. Absorbance of light at wavelength of 550 nm ($A_{550}$) by sample of culture from fermentor=50 to 60 at 24 hours.

2. Time Period: 24–32 Hours
   a. Temperature of medium.
      (1) 42° C. for 24–25th hours.
      (2) 40° C. for 25–32nd hours.
   b. Agitator speed: 1200 RPM.
   c. Energy input by agitator: 1.0–2.0 horsepower per 100 gallons.
   d. Aeration rate: 10 L (STP) per minute.
   e. Back pressure: 3–6 lbs per $in^2$.
   f. Dissolved oxygen: 10–40% of saturation. In order to obtain these values, the inlet air is enriched with oxygen and mixed prior to introduction to the fermentor through a sparger.
   g. Final absorbance: $A_{550}$ of 99–123.
   h. Additional feedings at 24 hours and at 29 hours.

Results

For HPLC analysis, fermentor broth samples were collected by centrifugation (10–15,000×g, 15 min.) and bacteria were resuspended in 3–5 volumes of buffered guanidine (8M guanidine HCl, 50 mM glycine NaOH buffer, pH 9.8, 5 mM reduced glutathione). The suspension was allowed to sit for 20–30 min. and was then homogenized (15–20 seconds) with a model SDT-1810

Tek-Mar tissue mizer. Insoluble debris was removed by centrifugation as above and the clarified BGH extract was assayed by HPLC.

The results obtained from three typical runs using the procedures specified above were as follows.

Final Assays of Fermentation Medium for Δ9 (Ser) BGH. Assay Method High Performance Liquid Chromatography (HPLC)

| Run No. | Back Pressure lbs per in$^2$ | Final Absorbance A$_{550}$ nm | Number of Cells per ml (Final) | Bovine Growth Hormone g/l (HPLC) |
| --- | --- | --- | --- | --- |
| 52 | 5 | 112 | 5 × 10$^{10}$ | 3.73 |
| 53 | 3 | 99  | 5 × 10$^{10}$ | 3.61 |
| 54 | 3 | 123 | 5 × 10$^{10}$ | 5.93 |

Level of expression 7×10$^6$ molecules of BGH per cell.

What is claimed is:

1. A method of producing bovine growth hormone which comprises: inoculating an aqueous fermentation medium with a transformant *E. coli* strain containing an expression vector which directs the expression of bovine growth hormone under the control of a phage lambda promoter-operator and an expression vector which directs the expression of the λcI857 temperature-sensitive repressor protein; growing the transformant strain in the fermentation medium for an initial growth period during which the level of dissolved oxygen in the medium is maintained at from 20% to 60% of saturation and the temperature of the medium is maintained at about 26° to 30° C.; raising the temperature of the fermentation medium to at least about 42° C. to inactivate the temperature-sensitive repressor protein, thereby initiating an induction period during which bovine growth hormone is produced; reducing the temperature to 38° C. to 41° C. and continuing to cultivate the transformant strain for the remainder of the induction period, during which the level of dissolved oxygen in the medium is maintained at from 10% to 40% of saturation; and recovering the bovine growth hormone from the transformant cells.

2. A method as claimed in claim 1, wherein the temperature is maintained at about 28° C. during the initial growth period.

3. A method as claimed in claim 1, wherein the temperature is reduced to about 40° C., following inactivation of the repressor protein, and maintained at about 40° C. for the remainder of the induction period.

4. A method as claimed in claim 1, wherein the level of dissolved oxygen in the medium is maintained at about 50% of saturation during the initial growth period.

5. A method as claimed in claim 1, wherein the initial growth period is effected for a period of from about 23 hours to about 25 hours.

6. A method as claimed in claim 1, wherein the initial growth period is effected for a period of about 24 hours.

7. A method as claimed in claim 1, wherein the induction period is effected for a period of about 7-8 hours.

8. A method as claimed in claim 1, wherein the temperature is increased to at least about 42° C. to induce production of bovine growth hormone when the cell density in the fermentation medium has reached an A$_{550}$ of from 50 to 60.

9. A method as claimed in claim 1, wherein the transformant strain is one which produces a biologically active fragment of bovine growth hormone in which the first 9 N-terminal amino acids are deleted and a serine residue is present at the N-terminus.

10. A method as claimed in claim 1, wherein the transformant strain is *E. coli* HB101 (P$_L$-mu-Δ9 (Ser) BGH and pcI857), ATCC 53030.

11. A method as claimed in claim 1, wherein nutrients are fed to the fermentation medium in portions at about 16, 24 and 29 hours after inoculation.

12. A method as claimed in claim 11, wherein about 45 to 60 grams of nutrients per fliter of fermentation medium are added to the medium about 16 hours and 24 hours after inoculation and about 20-25 grams of nutrients per liter of fermentation medium are added to the medium about 29 hours after inoculation, said nutrients comprising about equal amounts by weight of glycerol and an enzymatic casein hydrolysate.

13. A method as claimed in claim 1, wherein a first portion of nutrients is added to the fermentation medium when the cell density in the fermentor reaches an A$_{550}$ of from 30 to 35, a second portion of nutrients is added when the cell density reaches an A$_{550}$ of from 50 to 60 and a third portion of nutrients is added when the cell density reaches an A$_{550}$ of from 90 to 100.

14. A method as claimed in claim 13, wherein the nutrient portions comprise about equal amounts by weight of an enzymatic casein hydrolysate and glycerol.

15. A method as claimed in claim 14, wherein the first and second nutrient portions are added in an amount from about 45 to 60 grams per liter of fermentation medium and the third nutrient portion is added in an amount from about 20-25 grams per liter of fermentation medium.

16. A method as claimed in claim 1, wherein the dissolved oxygen level is maintained during the initial growth period by feeding ambient air to the fermentor at a rate of about 0.8 to 1.2 volumes of air (STP) per volume of liquid per minute and mechanically agitating the fermentation medium at about 1000 rpm with an agitator having a power input of about 0.5 to 2.0 horsepower per 100 gallons of fermentation medium.

17. A method as claimed in claim 16, wherein ambient air is fed to the fermentor at a rate of about 1.0 volume of air per volume of liquid per minute.

18. A method as claimed in claim 1, wherein the level of dissolved oxygen during said induction period is maintained at 10% to 40% of saturation by addition of oxygen to the inlet air being fed into the fermentor.

19. A method as claimed in claim 18, wherein the dissolved oxygen level is maintained during the induction period by feeding ambient air mixed with oxygen to the fermentor at a rate of about 0.8 to 1.2 volumes of air per volume of liquid per minute and mechanically agitating the fermentation medium at about 1200 rpm with an agitator having a power input of about 0.5 to 2.0 horsepower per 100 gallons of fermentation medium.

20. A method as claimed in claim 19, wherein ambient air is fed to the fermentor at a rate of about 1.0 volume of air per volume of liquid per minute.

* * * * *